(12) United States Patent
Denker et al.

(10) Patent No.: US 7,711,434 B2
(45) Date of Patent: May 4, 2010

(54) WIRELESS INTRAVASCULAR MEDICAL DEVICE WITH A DOUBLE HELICAL ANTENNA ASSEMBLY

(75) Inventors: Stephen Denker, Mequon, WI (US); Cherik Bulkes, Sussex, WI (US); Arthur J. Beutler, Greendale, WI (US)

(73) Assignee: Kenergy, Inc., Mequon, WI (US)

( * ) Notice: Subject to any disclaimer, the term of this patent is extended or adjusted under 35 U.S.C. 154(b) by 361 days.

(21) Appl. No.: 11/736,227

(22) Filed: Apr. 17, 2007

(65) Prior Publication Data

US 2007/0185538 A1    Aug. 9, 2007

Related U.S. Application Data

(62) Division of application No. 11/166,889, filed on Jun. 24, 2005, now Pat. No. 7,295,879.

(51) Int. Cl.
*A61N 1/08* (2006.01)
(52) U.S. Cl. .......................... 607/61; 607/32
(58) Field of Classification Search .......... 607/32, 607/36, 37, 38, 60, 61
See application file for complete search history.

(56) References Cited

U.S. PATENT DOCUMENTS

| | | | |
|---|---|---|---|
| 4,494,950 A | 1/1985 | Fischell | |
| 5,170,802 A | 12/1992 | Mehra | |
| 5,318,557 A * | 6/1994 | Gross | 604/891.1 |
| 5,411,535 A | 5/1995 | Fujii et al. | |
| 5,531,779 A | 7/1996 | Dahl et al. | |
| 5,713,939 A | 2/1998 | Nedungadi et al. | |
| 5,739,795 A | 4/1998 | Chanteau et al. | |
| 5,741,316 A | 4/1998 | Chen et al. | |
| 5,814,089 A | 9/1998 | Stokes et al. | |
| 5,954,761 A | 9/1999 | Machek et al. | |
| 5,967,986 A * | 10/1999 | Cimochowski et al. | 600/454 |
| 5,995,874 A | 11/1999 | Borza | |
| 6,026,818 A | 2/2000 | Blair et al. | |
| 6,067,474 A | 5/2000 | Schulman et al. | |
| 6,138,681 A | 10/2000 | Chen et al. | |
| 6,141,588 A | 10/2000 | Cox et al. | |
| 6,206,835 B1 * | 3/2001 | Spillman et al. | 600/485 |
| 6,231,516 B1 * | 5/2001 | Keilman et al. | 600/485 |

(Continued)

FOREIGN PATENT DOCUMENTS

WO        WO 01/63001        6/1999

(Continued)

*Primary Examiner*—Carl H. Layno
*Assistant Examiner*—Jon-Eric C. Morales
(74) *Attorney, Agent, or Firm*—Quarles & Brady LLP; George E. Haas

(57) ABSTRACT

A medical device, such as a cardiac pacing device for an animal, includes an intravascular antenna that has a first coil for engaging a wall of a first blood vessel to receive a radio frequency signal. The first coil includes a first winding wound helically in a rotational direction along a longitudinal axis from a first end of the coil to a second end. A second winding that is connected to the a first winding at the second end, is wound helically in the same rotational direction along the longitudinal axis from the second end to the first end. An electronic circuit is implanted in the animal and is connected to the antenna to receive an electrical signal therefrom.

10 Claims, 2 Drawing Sheets

U.S. PATENT DOCUMENTS

| | | |
|---|---|---|
| 6,431,175 B1 | 8/2002 | Penner et al. |
| 6,442,413 B1 | 8/2002 | Silver |
| 6,445,953 B1 | 9/2002 | Bulkes et al. |
| 6,505,072 B1 | 1/2003 | Linder et al. |
| 6,515,346 B1 | 2/2003 | Memeny |
| 6,516,230 B2 * | 2/2003 | Williams et al. ............ 607/116 |
| 6,561,975 B1 * | 5/2003 | Pool et al. ................... 600/300 |
| 2002/0005719 A1 | 1/2002 | Gilboa et al. |
| 2002/0026228 A1 | 2/2002 | Schauerte |
| 2002/0128546 A1 | 9/2002 | Silver |
| 2003/0135246 A1 * | 7/2003 | Mass et al. .................... 607/60 |
| 2003/0158584 A1 * | 8/2003 | Cates et al. ..................... 607/2 |
| 2004/0019364 A1 * | 1/2004 | Kieval et al. .................... 607/9 |
| 2005/0088357 A1 | 4/2005 | Hess et al. |
| 2006/0009856 A1 * | 1/2006 | Sherman et al. .......... 623/20.32 |

FOREIGN PATENT DOCUMENTS

| | | |
|---|---|---|
| WO | WO 99/26530 | 6/1999 |

* cited by examiner

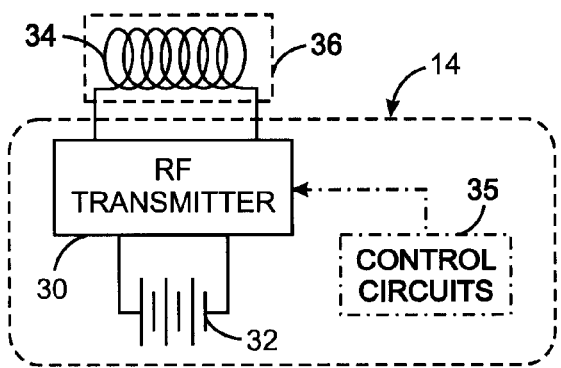
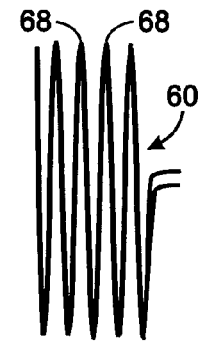
FIG. 6
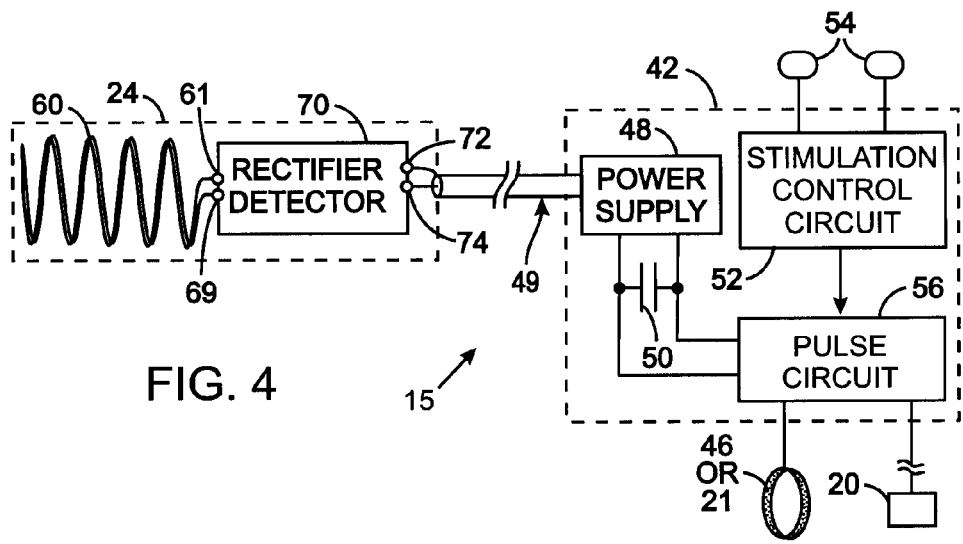
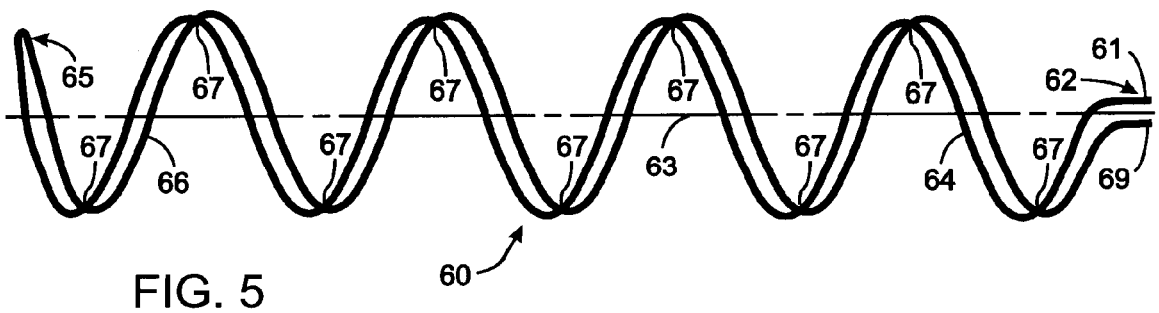
FIG. 5

WIRELESS INTRAVASCULAR MEDICAL DEVICE WITH A DOUBLE HELICAL ANTENNA ASSEMBLY

CROSS-REFERENCE TO RELATED APPLICATIONS

This application is a divisional of U.S. patent application Ser. No. 11/166,889 filed on Jun. 24, 2005, now U.S. Pat. No. 7,295,879.

STATEMENT REGARDING FEDERALLY SPONSORED RESEARCH OR DEVELOPMENT

Not Applicable

BACKGROUND OF THE INVENTION

1. Field of the Invention

The present invention relates to implantable medical devices which are controlled by a wireless signal that is received by the device, and more particularly to cardiac stimulation devices that are implantable in a vein or artery.

2. Description of the Related Art

A remedy for people with slowed or disrupted natural heart activity is to implant a cardiac pacing device which is a small electronic apparatus that stimulates the heart to beat at regular rates.

Typically the pacing device is implanted in the patient's chest and has sensor electrodes that detect electrical impulses associated with in the heart contractions. These sensed impulses are analyzed to determine when abnormal cardiac activity occurs, in which event a pulse generator is triggered to produce electrical pulses. Wires carry these pulses to electrodes placed adjacent specific cardiac muscles, which when electrically stimulated contract the heart chambers. It is important that the stimulation electrodes be properly located to produce contraction of the heart chambers.

Modern cardiac pacing devices vary the stimulation to adapt the heart rate to the patient's level of activity, thereby mimicking the heart's natural activity. The pulse generator modifies that rate by tracking the activity of the sinus node of the heart or by responding to other sensor signals that indicate body motion or respiration rate.

U.S. Pat. No. 6,445,953 describes a cardiac pacemaker that has a pacing device, which can be located outside the patient, to detect abnormal electrical cardiac activity. In that event, the pacing device emits a radio frequency signal, that is received by a stimulator implanted in a vein or artery of the patient's heart. Specifically, the radio frequency signal induces a voltage pulse in an antenna on the stimulator and that pulse is applied across a pair of electrodes, thereby stimulating adjacent muscles and contracting the heart.

The stimulator in that wireless system is powered by the energy of the received signal thus requiring that the pacing device transmit a relatively strong radio frequency signal in order to provide adequate energy to the stimulator implanted deep in the patient's chest. It is desirable to place the stimulator in a blood vessel located closer to the skin of the patient with stimulation electrodes implanted in one or more cardiac blood vessels and connected to the stimulator by wires extending through the electronic circuit circulatory system. This would enable more of the energy from the frequency signal to reach the stimulator, however, the blood vessels close to the skin are not sufficiently large to accommodate the size of the stimulator.

SUMMARY OF THE INVENTION

A medical device, such as a cardiac pacing device or an implanted defibrillator for example, includes an antenna assembly with an intravascular coil for engaging a wall of a first blood vessel to receive a radio frequency signal. The coil has a first end and a second end along a longitudinal axis. A first winding of the coil is wound helically in a rotational direction along a longitudinal axis from a first terminus at the first end to the second end, and a second winding connected to the a first winding at the second end and wound helically in that same rotational direction along a longitudinal axis from the second end to a second terminus at the first end.

The medical device also has an electronic circuit implanted in the patient and connected to receive an electrical signal from the receiver antenna assembly. In the case of a cardiac pacing device, the electronic circuit determines when stimulation of the heart is required and applies a voltage pulse to tissue of the heart.

The preferred embodiment of the medical device also includes a transmitter antenna outside the patient and a transmitter that generates a radio frequency signal which is applied to the transmitter antenna. The antenna assembly includes a detector that rectifies the radio frequency signal received from the transmitter antenna to produce a direct current. A storage device in the electronic circuit is connected to the detector for storing electrical energy derived from the radio frequency signal to provide electricity for powering other components of the electronic circuit.

Another aspect of the present invention is to implant the antenna assembly in a blood vessel of a limb or the neck of the patient and place the transmitter antenna so that it is positioned around the limb or neck. Ideally the longitudinal axis of the windings of the antenna assembly are substantially parallel with the axis of the transmitter antenna or its generated field to optimize signal coupling there between. A conductor extends from the antenna assembly through the patient's vascular system to the stimulator.

BRIEF DESCRIPTION OF THE DRAWINGS

FIG. 3 is a schematic diagram of a power source that transmits a radio frequency signal to the implanted components;

FIG. 4 is a schematic diagram of the implanted circuitry of the cardiac pacing apparatus;

FIG. 5 depicts the receiver antenna in a configuration during implantation; and

FIG. 6 illustrates the receiver antenna in a deployed configuration.

DETAILED DESCRIPTION OF THE INVENTION

Figure 1:
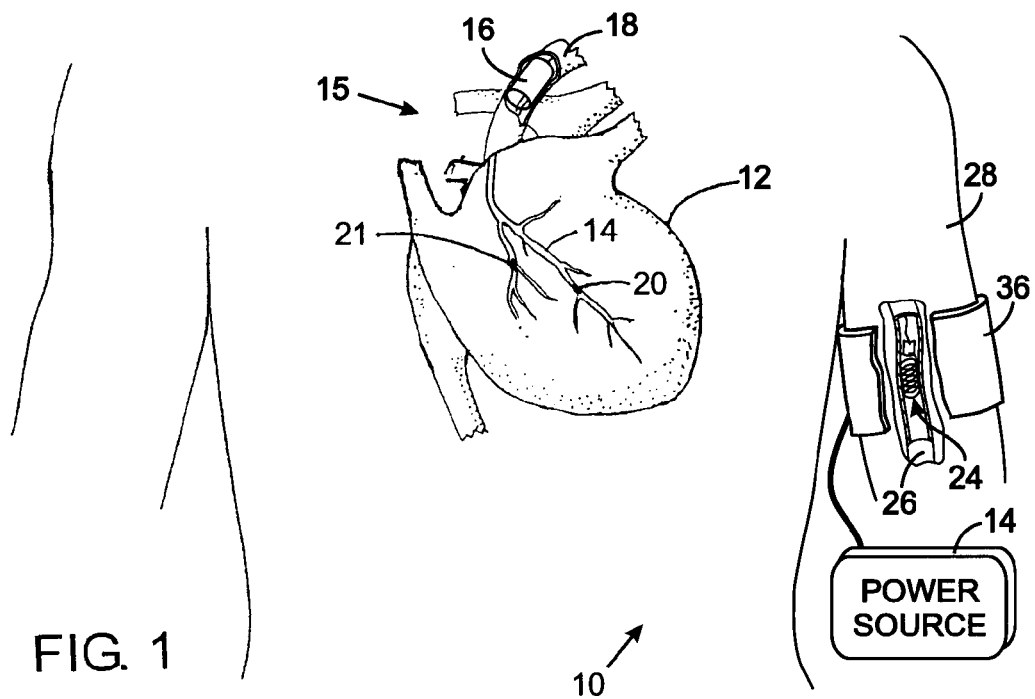
FIG. 1 is a representation of a cardiac pacing system attached to a medical patient.

With initial reference to FIG. 1, a cardiac pacing system 10 for electrically stimulating a heart 12 to contract comprises an external power source 14 and a pacing apparatus 15 implanted in the circulatory system of a human medical patient. The pacing apparatus 15 receives a radio frequency (RF) signal from the power source 14 worn outside the patient and the implanted electrical circuitry is electrically powered from the energy of that signal.

With additional reference to FIG. 3, the power source 14 comprises a radio frequency transmitter 30 that is powered by a battery 32. The transmitter 30 periodically emits a signal at a predefined radio frequency that is applied to a transmitter antenna 34. The transmitter antenna 34 is a coil of wire within a band 36 that is placed around the patient's upper arm 28. Thus the antenna coil is wound around the patient's arm. Alternatively another limb or area of the body, such as the neck, with an adequately sized blood vessel close to the skin surface of the human medical patient can be used. In a basic version of the cardiac pacing system 10, the radio frequency signal merely is used to convey energy for powering the pacing apparatus 15 implanted in the patient. In a more sophisticated version of the cardiac pacing system 10, the transmitter 30 modulates the radio frequency signal with commands received from optional control circuits 35 that configure or control the operation of the pacing apparatus 15.

Figure 2:
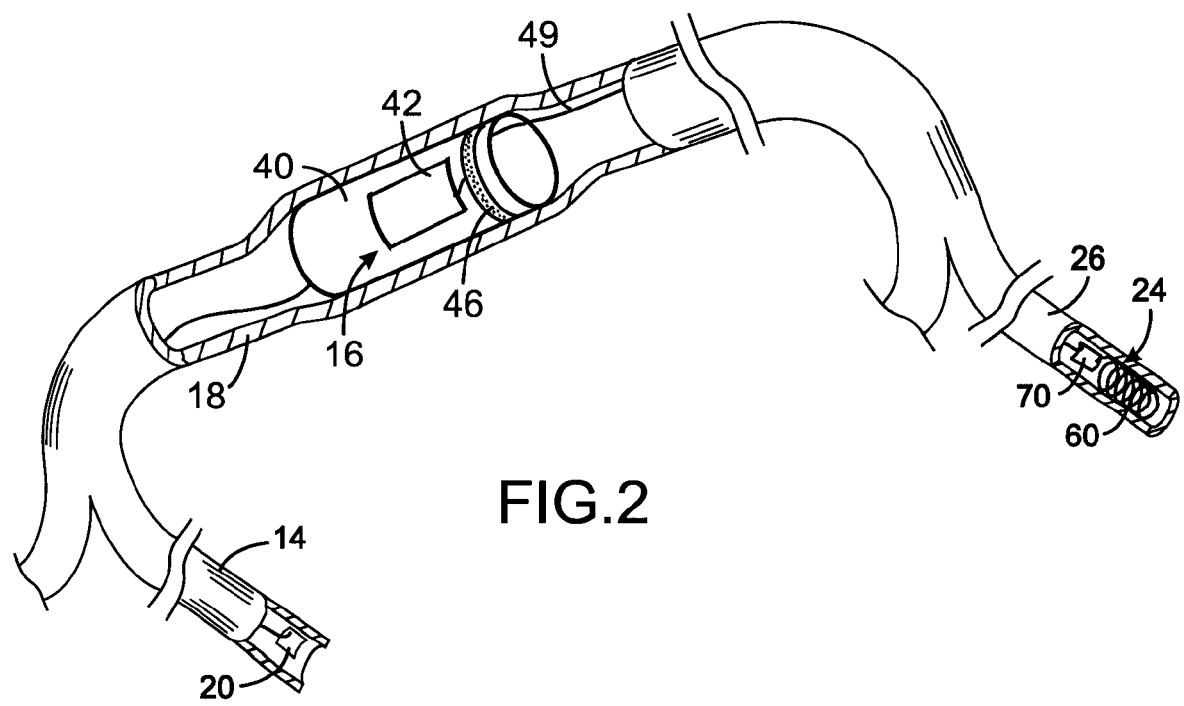
FIG. 2 is an isometric cut-away view of the patient's blood vessels in which an receiver antenna, a stimulator and a stimulation electrode have been implanted at different locations.

Referring to FIGS. 1 and 2, the implanted pacing apparatus 15 includes an intravascular stimulator 16 located a vein or artery 18 in close proximity to the heart. Because of its electrical circuitry, the stimulator 16 is relatively large requiring a blood vessel that is larger than the arm vein, e.g. the basilic vein which is approximately five millimeters in diameter. As a result, the stimulator 16 may be embedded in the superior or inferior vena cava. Electrical wires lead from the stimulator 16 through the cardiac vascular system to one or more locations in smaller blood vessels, e.g. the coronary sinus vein, at which stimulation of the heart is desired. At such locations, the electrical wires are connected to electrodes 20 and 21 implanted into the blood vessel walls.

Because the stimulator 16 of the pacing apparatus 15 is near the heart and relatively deep in the chest of the human medical patient, a receiver antenna 24 is implanted in a vein or artery 26 of the patient's upper right arm 28 at a location surrounded by the transmitter antenna 34 with the arm band 36. That arm vein or artery 26 is significantly closer to the skin and thus receiver antenna 24 picks up a greater amount of the energy of the radio frequency signal emitted by the power source 14, than if the receiver antenna was located on the stimulator 16.

As illustrated in FIG. 2, the intravascular stimulator 16 has a body 40 similar to well-known expandable vascular stents that are employed to enlarge a restricted vein or artery. Such vascular stents have a generally tubular design that initially is collapsed to a relatively small diameter enabling them to pass freely through a blood vessel of a patient. The stimulator body 40 and the other components of the pacing apparatus 15 are implanted in the patient's circulatory system using a catheter and techniques similar to those employed to implant vascular stents. In an additional embodiment, the stimulator 40 is encapsulated in a biocompatible waterproof capsule floating in the bloodstream of the vessel which has significantly larger diameter. From the capsule multiple micro-coaxial cables are connected to a plurality of bipolar electrodes in small cardiac blood vessels.

With reference to FIGS. 2 and 4, the stimulator body 40 has a pacing circuit 42 mounted thereon. Depending upon its proximity to the heart 12, the body 40 may have a stimulation electrode 46 in the form of a ring encircles the body. Alternatively, when the stimulator is relatively remote from the heart 12 the stimulation electrode 46 is replaced by a second stimulation electrode 21 (FIG. 1) located in a small cardiac blood vessel. The pacing circuit 42 includes a power supply 48 to which a micro-coaxial cable 49 from the receiver antenna 24 is connected. The power supply 48 utilizes electricity from that antenna to charge a storage capacitor 50 that provides electrical power to the other components of the pacing circuit 42. A stimulation control circuit 52, of a conventional design, detects the electrical activity of the heart by means of two or more sensing electrodes 54 located either on the stimulator body 40 or implanted in blood vessels of the heart 12. In response to that cardiac electrical activity, the stimulation control circuit 52 determines when electrical pulses need to be applied to the heart to stimulate cardiac contractions to provide a proper heart rate. When such stimulation is desired, the stimulation control circuit 52 sends a control signal to a pulse circuit 56 that applies electrical voltage from the storage capacitor 50 across the stimulation electrodes 20 and 21 or 46. Alternatively when bipolar electrodes are employed as devices 20 and 21, the electrical voltage is applied across the tissue contacts of each electrode.

The pacing apparatus 15 utilizes a unique receiver antenna 24. With reference to FIG. 5, the receiver antenna 24 comprises a coil 60 formed by an electrical conductor wound in a double helix. The coil 60 has a first terminus 61 at a first end 62 and a first helical winding 64 is wound in one rotational direction (e.g. clockwise) from that first terminus along a longitudinal axis 63 to an opposite second end 65 of the antenna coil. At the second end 65, the conductor loops into a second helical winding 66 that is wound in the same rotational direction going from the second end 65 back to the first end 62 where the second helical winding ends at a second terminus 69. Thus the conductor of the coil 60 is wound in the same direction when forming the double helix. However, viewed from either end of the coil 60, the first helical winding 64 extends from that end in one rotational direction and the second helical winding 66 extends from that same end in the opposite rotational direction so that convolutions of the helical windings cross each other. In the preferred embodiment illustrated in FIG. 5, the first and second helical windings 64 and 66 have the same number of turns which results in every convolution of each helical winding crossing the other helical winding at two locations 67. Although the size of the coil 60 and the number of turns may differ depending upon the particular application in which the antenna is being utilized, one application for an implantable pacing device employs a coil 60 that has a diameter of five to six millimeters, a length of two inches when deployed, and twelve turns in each helical winding 64 and 66.

The cross section of the wire used to wind the double helical coil 60 is selected to provide the desired spring coefficient. A coil made from round, or circular, wire has a uniform spring coefficient whereas a ribbon (wire with a rectangular cross section) exhibits different resistances to axial versus radial deformation. Various other cross sectional shapes can be used.

To implant the antenna 24 in a vein or artery of a patient, the coil 60 is stretched longitudinal which reduces its diameter, as depicted in FIG. 6. In this state the coil is releasably attached to a catheter that is used to guide and place the antenna 24 at the desired location within the patient's vascular system. When the antenna has been properly located, the catheter is operated to release the coil which, due to its resiliency, contracts longitudinally which increases its diameter, thereby springing into a shape illustrated in FIG. 5. When the coil 60 is in the deployed or contracted state the spacing between corresponding points 68 on adjacent convolutions is at least five times the width of the coil's conductor. In this expanded, or deployed, state the windings 64 and 66 are embedded into the wall of the blood vessel 26, as seen in FIG. 2, thereby securing the antenna 24 at that location. The antenna 24 is preferably embedded in an artery or vein in the upper arm of the patient wherein the longitudinal axis 63 of the receiver coil 60 is substantially parallel to the longitudinal axis or the field of the coil of the transmitter antenna 34 in the band 36 placed around the arm in FIG. 1. That alignment maximizes the signal coupling between the two antenna coils.

With reference to FIG. 4, the termini 61 and 69 of the antenna coil 60 are connected to the inputs of a rectifier detector 70 which converts the radio frequency signal received by the coil 60 into a DC voltage at the output terminals 72 and 74. Preferably the rectifier detector 70 is co-located with the antenna 24 in the arm 28 of the patient. The output terminals 72 and 74 are connected to a micro-coaxial cable 49 that extends through the patient's circulatory system to the power supply 48 in the circuit 42 of the intravascular stimulator 16. As previously described, the voltage received from the antenna 24 electrically powers the stimulator circuitry. By converting the radio frequency signal to a direct current at the remotely located antenna 24, the significant losses associated with sending a radio frequency signal in a wire extending through the vascular system are avoided.

The foregoing description was primarily directed to a preferred embodiments of the invention. Even though some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

The invention claimed is:

1. A medical device comprising:
 an antenna having a first coil adapted for engaging a wall of a first blood vessel of an animal to receive a radio frequency signal, wherein the first coil has a first end and a second end, and includes a first winding wound helically in a rotational direction along a longitudinal axis from a first terminus at the first end to the second end, and a second winding connected to the a first winding in a U-shaped section at the second end and wound helically in the rotational direction along the longitudinal axis from the second end to a second terminus at the first end;
 a detector connected to the first coil for converting the radio frequency signal into a direct current;
 an electrical storage device connected to the detector for storing electrical energy;
 a plurality of electrodes adapted to contact with at least one blood vessel of the animal;
 a stimulation control circuit which determines when stimulation of tissue of the animal is needed;
 a pulse circuit which responds to the stimulation control circuit by applying voltage from the electrical storage device across the plurality of electrodes; and
 a power source adapted for placement outside the animal and having transmitter antenna and a transmitter that generates the radio frequency signal which is applied to the transmitter antenna.

2. The medical device as recited in claim 1 wherein the detector is adapted for implantation in a first blood vessel adjacent the antenna, and the stimulation control circuit and pulse circuit are adapted for implantation in a second blood vessel and are connected to the detector by a conductor that is adapted to extend through the first blood vessel and the second blood vessel.

3. The medical device as recited in claim 1 wherein the transmitter antenna has a second coil that is wound along a given axis that is substantially parallel to the longitudinal axis of the first coil of the antenna.

4. The medical device as recited in claim 1 wherein each convolution of the first winding crosses the second winding.

5. A medical device comprising: an antenna assembly having a first coil adapted for engaging a wall of a first blood vessel of an animal to receive a radio frequency signal, wherein the first coil has a first end and a second end, and includes a first winding wound helically in a rotational direction along a longitudinal axis from a first terminus at the first end to the second end, and a second winding connected to the a first winding in a U-shaped section at the second end and wound helically in the rotational direction along the longitudinal axis from the second end to a second terminus at the first end;
 an electronic circuit adapted to be implanted in the animal remotely from the first blood vessel and connected to the antenna assembly to receive an electrical signal therefrom,
 wherein the electronic circuit comprises:
  (a) a detector connected to the first coil for converting radio frequency signal into a direct current:
  (b) an electrical storage device connected to the detector for storing electrical energy;
  (c) a plurality of electrodes adapted to contact with at least one blood vessel of the animal;
  (d) a stimulation control circuit which determines when stimulation of tissue of the animal is needed; and
  (e) a pulse circuit which responds to the stimulation control circuit by applying voltage from the electrical storage device across the plurality of electrodes; and
 a power source adapted for placement outside the animal and having transmitter antenna and a transmitter that generates a radio frequency signal which is applied to the transmitter antenna.

6. The medical device as recited in claim 5 wherein the antenna assembly further comprises a detector located adjacent and connected to the first coil for converting radio frequency signal into a direct current.

7. The medical device as recited in claim 5 wherein the transmitter antenna has a second coil that is wound along a given axis that is substantially parallel to the longitudinal axis of the first coil of the antenna assembly.

8. The medical device as recited in claim 5 wherein the transmitter antenna has a second coil that is adapted to be wound around a limb or neck of the animal.

9. The medical device as recited in claim 5 wherein the transmitter antenna has a second coil that is adapted to be affixed to the animal.

10. The medical device as recited in claim 5 wherein each convolution of the first winding crosses the second winding.

* * * * *